United States Patent [19]

Korpman

[11] 4,410,571
[45] Oct. 18, 1983

[54] ABSORBENT PRODUCTS, PROCESS AND COMPOSITIONS FOR IMMOBILIZATION OF PARTICULATE ABSORBENTS

[75] Inventor: Ralf Korpman, Bridgewater, N.J.

[73] Assignee: Johnson & Johnson, New Brunswick, N.J.

[21] Appl. No.: 274,232

[22] Filed: Jun. 22, 1981

Related U.S. Application Data

[63] Continuation-in-part of Ser. No. 181,289, Aug. 25, 1980, abandoned, and Ser. No. 248,387, Mar. 27, 1981.

[51] Int. Cl.$^3$ ............................................. A23L 2/02
[52] U.S. Cl. ............................ 427/385.5; 106/162; 106/205; 521/88; 521/89; 521/146; 521/149; 524/386; 524/388; 524/391
[58] Field of Search ............... 521/149, 146, 147, 88; 427/385.5; 524/386, 388, 391; 106/162, 205

[56] References Cited

U.S. PATENT DOCUMENTS

| | | | |
|---|---|---|---|
| 3,229,769 | 1/1966 | Pashaw | 169/1 |
| 3,347,236 | 10/1967 | Torr | 128/284 |
| 3,586,645 | 6/1971 | Granger et al. | 260/2.5 |
| 3,669,103 | 6/1972 | Harper et al. | 128/156 |
| 3,670,731 | 6/1972 | Harmon | 128/284 |
| 3,686,024 | 8/1972 | Nankee et al. | 117/140 A |
| 3,850,652 | 11/1974 | Asako et al. | 106/197 R |
| 3,888,257 | 6/1975 | Cook et al. | 128/296 |
| 3,900,030 | 8/1975 | Bashan | 128/285 |
| 3,926,891 | 12/1975 | Gross et al. | 260/29.6 E |
| 3,935,099 | 1/1976 | Weaver et al. | 210/43 |
| 3,957,362 | 5/1976 | Mancini et al. | 521/149 |
| 4,049,764 | 9/1977 | Sigl et al. | 264/178 F |
| 4,078,568 | 3/1978 | Etes et al. | 128/283 |
| 4,079,021 | 3/1978 | Coupek et al. | 521/155 |
| 4,102,340 | 7/1978 | Mesek | 128/284 |
| 4,103,062 | 7/1978 | Abersen et al. | 428/283 |
| 4,105,033 | 8/1978 | Chatterjee et al. | 128/285 |
| 4,134,863 | 1/1979 | Fanta et al. | 260/17.4 |
| 4,156,664 | 5/1979 | Skinner et al. | 260/17.4 GC |
| 4,232,674 | 11/1980 | Melican | 128/287 |
| 4,235,237 | 11/1980 | Mesek | 128/284 |

FOREIGN PATENT DOCUMENTS

| | | |
|---|---|---|
| 26988 | 9/1980 | European Pat. Off. |
| 2004201A | 3/1979 | United Kingdom |
| 1557254 | 12/1979 | United Kingdom |
| 2046773A | 11/1980 | United Kingdom |
| 2063283A | 6/1981 | United Kingdom |

OTHER PUBLICATIONS

Chemical Week, Jul. 18, 1979, p. 40.

*Primary Examiner*—Morton Foelak
*Attorney, Agent, or Firm*—Leonard Kean; Alice O. Robertson

[57] ABSTRACT

Particulate absorbents of a water-insoluble water-swellable polymer having a gel capacity of at least 10 are immobilized with a composition comprising the absorbent in a liquid polyhydroxy organic compound. The composition may be employed by applying to an appropriate surface and subjecting the liquid film to solidifying conditions. The solidified film product has high absorptive capacity and is free of undesirable movement when positioned in absorbent articles.

A foam product having both absorptive and cushioning properties is prepared from a solid, particulate, water-insoluble, water-swellable polymer having a gel capacity of at least 10, a solid, particulate blowing agent, and a liquid polyhydroxy organic compound. Foamable compositions and articles employing the foam are also described.

28 Claims, No Drawings

ABSORBENT PRODUCTS, PROCESS AND COMPOSITIONS FOR IMMOBILIZATION OF PARTICULATE ABSORBENTS

This is a continuation-in-part application Ser. No. 181,289, filed Aug. 25, 1980, now abandoned and Ser. No. 248,387 pending, filed Mar. 27, 1981.

The present invention relates to absorbent products, compositions and methods for immobilizing particulate absorbents and absorbent articles produced therefrom.

Absorption of mobile aqueous liquids have conventionally been accomplished by the use of sponge or batting. More recently, water-insoluble but water-swellable polymers having high absorptive capacity have been developed for immobilizing water and aqueous fluids. These polymers are particulate, i.e., pulverulent or granular and have no structural integrity. They are frequently referred to in the art as "superabsorbents," "hydrogels" or "hydrocolloids" and have been incorporated in the cellulosic absorbent structure in diapers, sanitary napkins and other absorbent articles to increase their absorptive efficiency. The expected advantage of incorporating these particulate materials is diminished by the shifting of the particulate materials generally requiring special construction to immobilize them within the structure of the articles. A process for decreasing the mobility of particulate absorbent materials and products in which the particulate absorbents are uniformly retained is desirable. In U.S. Pat. No. 3,900,030, there is described a catamenial tampon which utilizes an open-celled polymer foam which has the water-swellable polymers imbedded therein. While this provides structural integrity to the absorbent polymer, versatility in application is governed by the foam carrier. Moreover, the method of disposition is dictated by the foam carrier.

DESCRIPTION OF THE INVENTION

In accordance with the present invention it has been discovered that by mixing together a particulate, water-insoluble water-swellable polymer absorbent and a liquid polyhydroxy organic compound the polymer absorbent may be immobilized. Immobilizing compositions comprising the polymer absorbent and liquid polyhydroxy organic compound may be employed to form novel products in which the absorbent has been converted to a non-particulate immobilized form, i.e., an absorbent bearing solidified structure. When the composition includes a blowing agent, the composition is a foamable immobilizing composition and the absorbent bearing solidified structure is a foam product. In the absorbent-immobilizing compositions, at least 25 to no greater than 125, preferably from about 40 to 80 parts by weight of the polymer absorbent are employed for every 100 parts by weight of the liquid polyhydroxy organic compound. The composition suitable for the preparation of foam products contain in addition from about 2 to about 30 parts by weight of blowing agent. The absorbent-immobilizing composition with or without blowing agent (a) may be cast, coated or cold extruded on an appropriate surface to obtain free films or sheets, (b) may be coated on the ultimate surface, e.g., substrate to form a film coating or (c) if a foam-forming composition, also may be foamed in place. The products have structural integrity on solidification, have superior absorptive efficiency, are self-supporting, and are degradably disposable as hereinafter described.

The absorbent products are structurally stable solids, resilient and somewhat elastic, which rapidly swell on absorption of fluid. They have the property of being degradable in large excess of water to water-dispersible particles, providing a convenient means for disposition after the desired function has been accomplished. When the absorbent product is a foam product, it differs from conventional sponge or solid foam in having an extremely high capacity for absorbing aqueous fluids, being limited by the absorptive capability of the polymer absorbent and not by the dimensions of the original foam structure. The products are also advantageous in being easily prepared from a non-toxic liquid foam-forming composition which is readily manageable without the necessity of adding water or organic solvent. Absorbent articles having particulate absorbents immobilized by an absorbent-bearing solidified structure according to the present invention have high absorptive capacities which are not diminished by shifting and bunching of particulate absorbents accompanying transportation and handling prior to use. Moreover, the rate of absorption is substantially undiminished by the presence of a solidified structure enveloping the absorbent particles. The uptake of aqueous liquid is substantially instantaneous. This is wholly unexpected inasmuch as the presence of a carrier usually decreases the absorption rate.

The absorbent products are useful as the sole or supplementary absorbent panel material in absorbent articles such as bed pads, sanitary products, diapers, incontinence pads and the like. When the absorbent product is to be used as the sole absorbent panel, it may be applied directly to the ultimate substrate to be employed in the absorbent article, e.g., a diaper backing. Substrates suitable for such purposes include, for example, film such as polyethylene film, non-woven cellulosic materials, wood-pulp materials and the like. However, it may be employed in combination with wood-pulp panels used in batting and with other absorbent materials while still having the effect of reducing size or thickness. The product when foam, not only has superior absorptive capabilities but has a soft feel and resilience thereby providing comfort without the thickness of conventional batting. A related application employing the absorbent product, especially in the form of foam, on a flexible substrate is in medical or surgical dressings and sponges.

When the product is a foam, its resilient and somewhat elastic nature renders it also useful in applications where both absorption and cushioning is desired such as in packaging, particularly for odd shape structures. Since the foam may be prepared from nontoxic materials, it is readily adaptable to foaming-in-place. However, the foam is stable and may be prepared in any size and shape, and stored with or without supporting structure. If desired it may be cut to the desired form for ultimate use.

An application of combined absorption and cushioning use is as a protective liner in dual-walled or dual containers for transporting aqueous fluids in which the inner wall or inner container is of breakable material such as glass used in transporting radioactive solutions or biological fluids. If the containers require special materials such as outer lead containers for radioactive fluids, it is desirable to reuse the lead container; the foam product is advantageous in being readily removable from the container by flushing the container with excess water.

The expression "absorbent" refers to water-insoluble, water-swellable polymers as hereinafter described having an enhanced capacity for removing water or aqueous fluids. The water-insoluble, water-swellable polymers are lightly cross-linked polymers containing a plurality of hydrophilic groups, such as carboxyl, carboxamide, sulfonate salt or hydroxyl groups, along the polymer chain in sufficient proportions so that the polymer would be water-soluble if it were not for the cross-linking thereof. In these polymers, the hydrophilic groups constitute at least twenty-five percent and up to seventy-two percent of their molecular structure. The materials are of sufficient molecular weight or degree of cross-linking to be water-insoluble while being water-swellable. Many of the suitable materials are those which have been reported to have an average molecular weight per cross-linkage in the range of from about 13,000 to about 300,000, but are not limited thereto. The most common and best known of such materials are polyacrylate modified polysaccharides, cross-linked synthetic polyacrylates, cross-linked carboxymethylcelluloses or cross-linked poly(alkylene oxide)s as hereinafter defined. Other graft polymers of polysaccharides and natural gums such as xanthan gum, locust gum, guar gum and the like or blends thereof are also suitable provided they meet the requirements of water insolubility and water swellability. The water-insoluble, water-swellable polymers have a gel capacity of at least about 10. By "gel capacity" is meant the weight of aqueous fluid which can be imbibed and held per unit weight of polymer, i.e., grams of fluid per gram of polymer. Stated another way, the absorbent polymers have an absorbent capacity of at least 10 times the weight of the material in dry form. The capacity may be up to 1500 times or more of the weight of the material in dry form; commonly it is about 15 to 70 times the dry weight. The materials are frequently spoken of in the art as "hydrogels", "hydrocolloids" or "superabsorbents". Many of the water-swellable polymers are available commercially.

The polymers are used in particulate form. By "particulate" is meant a substance in the form of fine discrete particles. They may be variously shaped such as spherical, rounded, angular, acicular, irregular, or fibrous. The particles generally range in size from about 1 micron to $2 \times 10^4$ microns in diameter or cross-section (largest dimension when not spherical). The particles are preferably of finely divided powder of particles size of from about 1 to about $10^3$ microns.

By "absorbent-immobilizing composition" is meant a composition containing a water-insoluble water-swellable polymer in particulate form and a liquid polyhydroxy organic compound and which may contain a blowing agent and/or minor amounts of non-essential additives hereinafter detailed. The composition is the vehicle for immobilizing particulate absorbent.

The liquid polyhydroxy organic compound employed in the present invention is a high boiling liquid having at least two hydroxy groups, preferably vicinal or adjacent hydroxy groups. Suitable liquids include glycerol, ethylene glycol, propylene glycol, and the like. Glycerol and ethylene glycol are preferred.

The blowing agent in the foamable absorbent-immobilizing compositions may be any non-gaseous agent decomposing to form a gas and includes sodium bicarbonate, azo compounds, such as azodicarbonamide, p-toluenesulfonyl semicarbazide, p,p-oxybisbenzenesulfonyl hydrazide, p-toluenesulfonyl hydrazide and the like. In certain aspects of the present invention, a non-foamable absorbent-immobilizing composition may be employed and the blowing agent may be a gas such as air, nitrogen, carbon dioxide and the like.

In addition to the foregoing components, the composition may have included therein minor amounts of other additives which may impart desirable properties to the absorbent product. Thus, a surface active wetting agent, particularly non-ionic surface active agent may be included to enhance liquid uptake. A surface active agent is of particular advantage in assisting vertical transport of liquids. Representative surface active agents are those commonly described such as alkyl aryl polyether alcohols or alkylphenyl ethers of polyethylene glycol, e.g., reaction product of t-octylphenol or nonylphenol with ethylene oxide. Fine fibrous cellulose such as cellulose flour, silicates and the like also have similar effect. Activated charcoal or other adsorbent may be included for odor uptake. Fragance, coloring, etc., may be included for a pleasing effect. Inert materials containing bound water such as silicates, aluminum hydrate and the like may be employed to modify the texture of the sheet. Similar results may be achieved employing slightly wet ethylene glycol or glycerol, e.g., commercial glycerine. If the absorbent immobilizing composition contains a low level of pulverulent absorbent, there is a slight tendency for the absorbent to settle. The composition may be modified to include small quantities of materials to affect its spreading properties. Suitable viscosity modifiers include silicated powders, clays, zinc oxide, inert fillers and like materials. Also, the polyhydroxy compounds may be modified with minor amounts of liquid modifiers such as ether glycols, mineral oil, etc., not contemplated as the essential component of the instant compositions. Generally, the additives, if employed, do not constitute more than about 25 percent of the total composition.

By "absorbent-bearing solidified structure" is meant the solid resulting on solidification of the liquid composition after application to a substrate or carrier surface, or to a metal or release coated surface for free film, sheet or foamed sheet formation, or also if foamable composition after application to a container. When the absorbent bearing solidified structure is a film or sheet, whether foam or non-foam, it may be in the form of a continuous film or a discontinuous one; it may have a lattice-like form. Also, as hereinafter described, it may be in the form of a filament. The term "film" as herein employed contemplates a thickness up to about 10 mils. The term "sheet" contemplates a thickness greater than 10 mils and may be non-foam or foam. Preferred structures are sheets, both foam and non-foam.

The process of immobilizing particulate absorbent and foaming an absorbent bearing solidified structure is carried out by applying an absorbent-immobilizing composition comprising an absorbent and a liquid polyhydroxy organic compound, prepared by mixing the components together onto a temporary or ultimate surface. The amount of absorbent employed depends in part on the viscosity of the liquid polyhydroxy organic compound used as vehicle as well as on the amount desired in the ultimate product while within the range previously set forth.

When the absorbent bearing solidified structure is a foam, it may be prepared by mixing the components in any sequence to obtain an absorbent-immobilizing foamable composition and then subjecting the composition to foaming conditions to obtain the desired foam product. Thus, it may be prepared by first mixing together an appropriate water-insoluble, water-swellable polymer and blowing agent, thereafter adding a liquid polyhydroxy organic compound to the dry mixture and then stirring until homogeneous to obtain a foamable absorbent-immobilizing composition. Alternatively, the polymer and the liquid polyhydroxy organic compound may be mixed together and the blowing agent thereafter added to obtain a foamable absorbent immobilizing composition. A foam structure also may be prepared from a non-foamable composition as subsequently detailed.

Compositions of polymer absorbent in liquid polyhydroxy organic compound have time-limited fluidity and mobility. They are preferably prepared within several hours prior to use or at least within 24 hours but some absorbent-immobilizing compositions remain the liquid form for longer periods.

The liquid absorbent-immobilizing composition then may be applied to a temporary or ultimate surface. The ultimate surface is hereinafter referred to as substrate. For making a film, sheet, foam sheet or coated substrate, any method of application conventionally employed for coating or preparing films, e.g., knife-coating, spray-coating, reverse-roll coating, gravure-coating, cold extrusion coating or casting, and the like, may be employed. Preferred methods are cold extrusion coating and knife-coating. The cold extrusion coating method may be employed to prepare a foam structure from the immobilizing composition which does not contain a particulate blowing agent. In this procedure, inert gas as blowing agent is injected downstream into the extruder chamber at a point where mixing has been completed to foam the mixture and to produce a viscous foamed extrudate which then may be coated in any manner. Another method of making a foam structure from an immobilizing composition which does not contain a blowing agent is to whip air into said composition and thereafter coating in any manner.

When use as a coating on a substrate is contemplated, the substrate is of materials generally employed for absorbent articles, such as cellulose, vinyl films, polypropylene, polyester, polyethylene, nylon, metal foils, elastomers, cloth, nonwovens of various fibers, and the like. Coating on a substrate may be of the entire surface of the substrate, in strips or in any other pre-determined pattern. When use as a free film, sheet or foam sheet is contemplated, the coating may be made on material previously coated with a release agent such as silicone or on a metal surface. When the immobilized absorbent structure is foam to be used in an irregularly shaped device, the liquid composition may be poured into the irregularly shaped area. The coated substrate, the coated sheet-forming surface, or the foamable composition contained in an irregularly shaped device is then subjected to time-temperature related conditions to transform the liquid composition into a solid immobilized absorbent structure in the form of a film, sheet, coating or foam product.

The conversion of the liquid absorbent-immobilizing composition from a liquid-solid mixture to a solid film, sheet or foam may take place at a temperature up to 175° F. in a period as short as 15 minutes but more usually over a period from about 30 minutes to 24 hours, or at elevated temperatures, 175° F. to 450° F. (79° C. to 111° C.), preferably about 275° F. to 400° F. (135° C. to 204° C.) for a period of from a few seconds up to about 15 minutes. In producing foam, the foamable immobilizing composition may be placed in an appropriate vessel or onto a substrate or surface for foaming, and allowed to foam at the appropriate temperature. Where speed is desired, transformation of the liquid composition to a solid may be accomplished by exposure to heat in the range of about 200° F. to 450° F. (93° C. to 111° C.) for about 1 to 60 seconds.

A factor affecting rate of solidification in addition to temperature is the amount of polymer absorbent. Compositions with high absorbent content, e.g., greater than about 50 parts per 100 parts of liquid polyhydroxy compound, solidify at ambient temperature in time measured in hours but with lower amounts of absorbent, there is increase in the time necessary for completion of a solidified structure formation. The solidified structure has been found to be more quickly formed from the more viscous liquid polyhydroxy compounds. However, the ultimate polymer absorbent content of the solidified structure is generally lower with the more viscous polyhydroxy compound since it is difficult to form a homogeneous composition. Thus, for example, a film or foam obtained from glycerol as polyhydroxy compound generally has less absorbent than that from ethylene glycol as polyhydroxy compound. However, as previously indicated, for maximum absorptive efficiency of the ultimate product, it is desirable that the liquid polyhydroxy compound be the major component. Preferred films or sheets, whether foamed or not, are those containing from about 40 to 80 parts by weight of absorbent per 100 parts by weight of polyhydroxy compound.

The particulate absorbent in the absorbent-bearing solidified structure is firmly retained in the film or lattice and is not subject to moving or shifting in the ultimate absorbent article and retains all the high absorptive capacity of the particulate absorbent.

The liquid absorbent-immobilizing composition particularly without blowing agent, in addition to being useful as starting material for the solidified absorbent bearing film or structure above described, is also useful in the liquid form and may be applied to dressings, skin, body exudates as well as to aqueous liquids from other sources.

Many water-insoluble, water-swellable polymers suitable as absorbent are available commercially. They also may be prepared by cross-linking a pre-formed water-soluble, straight chain polymer, by polymerizing an appropriate monomer or a monomer with a co-monomer to effect simultaneous polymerization and cross-linking, or by incorporating a hydrophilic group into a completed polymer. An example of a later incorporation of a hydrophilic group to the completed polymer is the incorporation by sulfonation of a sulfonic acid moiety. When it is desired to have the hydrophilic group in the salt form, the polymer may be prepared first as an acid, ester, amide, or nitrile and the product hydrolyzed in whole or in part.

The preferred polymers have an acrylate group in their molecular structure. They may be completely synthetic acrylate polymers or acrylate modified polysaccharides, e.g., acrylate modified starch or acrylate modified cellulose. By "acrylate modified" is meant that an acrylate polymer or polyacrylate as hereinafter described has been grafted onto the polysaccharide. "Acrylate polymer" or "polyacrylate" as herein employed embraces not only polymers which contain acrylate salt groups but those which also may contain an acrylamide, acrylic acid, acrylic ester group or acrylonitrile group.

The preferred synthetic acrylate polymer absorbents are those which have a salt group, an acid group, or which have both an amide group and a salt or acid group. These have been represented in the literature, e.g., U.S. Pat. No. 3,686,024, by the following formula:

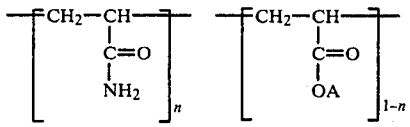

where A is an alkali metal ion such as sodium or potassium, or is hydrogen, n is from about 0.5 to about 0.9, 1−n defines the extent of hydrolysis, and z is the number of mer units between cross-links.

The polyacrylate absorbent containing both amide and carboxylate groups may be prepared either (1) by aqueous polymerization of acrylamide with a difunctional organic cross-linker such as N,N'-methylenebisacrylamide in the presence of a free radical catalyst to obtain a water-swellable, cross-linked polyacrylamide, followed by partial hydrolysis in aqueous alkali to obtain a cross-linked polymer having both an amide and an alkali metal carboxylate groups as more fully described in U.S. Pat. No. 3,247,171, or (2) by copolymerization of acrylamide and acrylic acid alkali metal salt in the presence of a cross-linking monomer such as N,N'-methylenebisacrylamide and a catalyst system such as 1:1 ammonium persulfate and β-dimethyl-aminopropionitrile, also described in the aforesaid patent, or (3) by radiation polymerization and cross-linking as described in U.S. Pat. No. 4,192,727.

Polyacrylate absorbents also may be prepared by subjecting linear polyacrylate to high energy radiation cross-linking as described in U.S. Pat. No. 3,229,769, or to chemical polymerization and cross-linking as described in British Pat. No. 719,330, or may be prepared by cross-linking of a previously prepared polyacrylamide.

Acrylate modified polysaccharides are those which have a polyacrylate chain grafted onto a cellulose or starch molecule. They are preferred graft copolymers of polysaccharides which have hydrophilic chains grafted thereon. By "hydrophilic chain" is meant a polymer chain obtained from monomers which have a group which is water-soluble or becomes water-soluble or hydrolysis, e.g., carboxyl, sulfonic, hydroxyl, amide, amino, quaternary ammonium and hydrolysis products thereof. In the polysaccharides acrylate polymers, a hydrophilic chain of the general formula

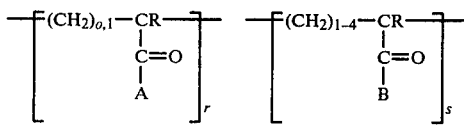

is attached to the backbone of the cellulose or starch molecule through a carbon linkage. In the formula,

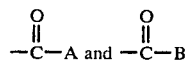

independently represents an acid, ester, alkali metal, ammonium salt or amide group, each R independently is hydrogen or lower alkyl, r is an integer of from 0 to about 5,000 and s is an integer of from 0 to about 5,000, and r+s is at least 500.

The polysaccharide acrylate polymers may be prepared employing well known procedures for carrying out graft copolymerization of olefinically unsaturated chains onto cellulose and starch in which grafting of the hydrophilic material onto a starch or cellulose backbone is accomplished simultaneously with the formation of the hydrophilic polymeric material, and, if necessary, followed by hydrolysis. Thus, the polymers may be prepared by the polymerization of an appropriate polysaccharide with an appropriate acrylic monomer such as acrylonitrile, methacrylonitrile, methyl or ethyl acrylate, acrylic or methacrylic acid, or with acrylamide or methacrylamide, followed by alkaline hydrolysis or by the polymerization of alkali metal salt of acrylic or methacrylic acid with the appropriate polysaccharide.

The polymerization is carried out in the presence of a free radical catalyst system in an aqueous medium, or by irradiation (ultra-violet, gamma-, or X-radiation). Catalyst systems for employment in aqueous media usually comprise an inorganic oxidizing agent as initiator and an inorganic reducing agent as activator. Representative oxidizing agent initiators are inorganic persulfates, peroxides and alkali metal bromates and chlorates. Representative reducing agent activators are alkali metal bisulfites, sulfites, ferrous ammonium sulfate, and alkali metal thiosulfate.

In a method for carrying out graft polymerization employing a catalyst system, the inorganic oxidizing agent initiator and the inorganic reducing agent activator each as an aqueous solution are alternately added to a reaction medium comprising a water-solution of an acrylate monomer, a co-monomer, a cross-linking monomer, and a dispersion of pulverulent or fibrous water-insoluble water-swellable polysaccharide in water-immiscible organic liquid containing a minor amount of water-miscible solvent to obtain an acrylate modified polysaccharide product as more fully described in U.S. Pat. No. 4,028,290. Other suitable methods for chemical catalytic graft polymerization may be found in U.S. Pat. Nos. 3,256,372; 3,661,815; 4,076,663; 3,889,678 and 4,105,033.

Suitable polysaccharide acrylate polymers are those in which the hydrophilic chain loading on the backbone is in the range of from about 10 percent by weight to about 90 percent by weight, usually from about 40 to 80 percent by weight of the polysaccharide acrylate polymer.

Other suitable water-insoluble, water-swellable polymers include cross-linked carboxymethylcellulose (CMC) obtained as described, for example, in U.S. Pat. No. 2,639,239, cross-linked poly(alkylene oxide) of molecular weight of at least 100,000, obtained as described, for example, in U.S. Pat. Nos. 3,956,224; 3,264,202; 3,957,605 and 3,898,143; and blends of organic substances of polysaccharide character, e.g., natural or synthetic gums. It has been found generally that when gums are employed they must be employed as blends. It appears that the polysaccharide gums which are normally soluble interact when employed as blends to have the desirable swellability without the undesirable solubility. Typical gums which may be employed in blends include locust bean gum, guar gum, xantham gum, tragacanth gum, karaya gum and the like. Gum blends as well as the absorbent polymers above described are available commercially under various trade names.

The water-insoluble, water-swellable polymers prepared by any of the foregoing methods are generally obtained as stiff, brittle solids. These may be comminuted to the appropriate size. Preferably they are employed in the form of powder as previously defined, but may also be employed in other forms.

The liquid polyhydroxy compounds which are suitable from the currently available hydroxy compounds are quite limited and are substantially as previously defined. Commercial grades of vehicles are appropriate. It is not necessary to subject them to drying prior to use. Although liquids such as propylene glycol are operable in forming the desired film, the slowness in forming the film renders them less desirable in the invention directed to a process for immobilization.

When the solidified structure is a film or a foam sheet, it may be only part of a moisture receiving component of the absorbent article. However, as previously indicated, it may be obtained as a free film or foam sheet and be employed in the ultimate absorbent article to constitute the entire moisture receiving portion thereof. It may be used wherever a dessicant is necessary.

The absorbent product as a free absorbent film or sheet is preferably formed by casting on a metal surface or coating on a silicone or other release agent covered surface a liquid absorbent-immobilizing composition comprising from about 25 to 125 parts of particulate absorbent polymer in 100 parts of liquid polyhydroxy organic compound and allowing the liquid composition to solidify either by heating at temperatures of from 175° F. to 450° F. for from a few seconds to about 15 minutes or standing at temperature up to 175° F. for from about 30 minutes to about 24 hours. The absorbent product as a coating on a substrate is formed by coating on the ultimate substrate under similar conditions.

The absorbent product as a solidified structure may be in the form of filament or rope. Such form may be achieved readily by metering absorbent and polyhydroxy compound into a cold extruder with the die heated to a temperature in the range of 175° F. to 450° F. and recovering the extruded filament or rope.

The preferred absorbent product as an immobilized structure is in the form of foam. The foam product in the shape of a sheet is preferably obtained by casting or coating on metal surface or on a silicone or other release agent coated roll surface a liquid absorbent-immobilizing composition comprising from about 25 to 125 parts of particulate absorbent polymer and 2 to 30 parts by weight of blowing agent for 100 parts by weight of liquid polyhydroxy organic compound, and allowing the coated liquid composition to stand at temperatures up to about 175° F. for from about 30 minutes to 24 hours, or by heating the coated composition from 175° F. to 450° F. for from a few seconds to about fifteen minutes.

When the absorbent product is a foam product to be employed as a protective liner of a dual-walled container, the liquid immobilizing absorbent composition is poured into the area between the container walls and allowed to stand at ambient temperature or heated as for the foam sheets.

The actual amounts of absorbent in the compositions within the scope previously indicated is dependent on the level of absorption required in the ultimate environment. Thus, if the absorption is to be accomplished by a diaper, and the substrate is a diaper pad, the liquid absorbent immobilizing composition with or without blowing agent will contain absorbent sufficient to supply the desired absorptive capacity to the pad substrate. The products and processes are useful in the manufacture of numerous absorbent articles. They are especially useful where reduction in bulk of absorbent as well as high capacity is desirable, such as in articles to be worn. Thus, they are particularly useful for diapers and incontinence pads, but also for sanitary napkins, bandages and the like. Both the film and foam form of the product are useful although the latter is preferred. In use in diapers, the absorbent product may be as a sole absorbent or as a component improving the quality of the existing absorbent. In the manufacture of diapers in which the film or foam product is incorporated as a improvement to the liquid receiving portion of the diaper, the composition is applied to the surface of the aqueous liquid receiving portion of the article, namely batting, the coated batting subjected to a heating cycle or to standing at temperatures up to 175° F., and the resulting modified batting provided with moisture impermeable backing and a moisture permeable top sheet. Alternatively, the absorbent immobilizing composition may be coated on a conventional non-absorbent moisture impermeable diaper backing without batting and thereafter laminated with a conventional moisture permeable top sheet to provide a thin diaper. The foam product is particularly adaptable to this use. Other techniques within the skill of those to whom the invention is directed may be employed to obtain new absorbent diapers.

In the case of sanitary napkins, the absorbent immobilizing composition may be applied to the cellulosic absorbent surface and wrapped in a conventional manner to produce a napkin of improved absorptive capacity.

In the case of bandages, the absorbent composition may be coated onto an aqueous liquid permeable but a gel impervious materials, e.g., non-woven fabrics such as of rayon or polyester fabrics, and then inserted in the gauze bandage.

The following examples illustrate the invention but are not to be construed as limiting:

EXAMPLES I–VIII

Absorbent compositions set forth in Table A are prepared.

TABLE A

| Component | Amount of Components (parts by weight) Examples | | | | | | | |
|---|---|---|---|---|---|---|---|---|
| | I | II | III | IV | V | VI | VII | VIII |
| Absorbent | | | | | | | | |
| Starch Polyacrylate,+ (SGP 502S, Henkel) | 50 | | | | | | | |
| Starch Polyacrylate+ (Stasorb ®, A. E. Staley) | | 25 | | | | | | |

TABLE A-continued

|  | Amount of Components (parts by weight) Examples | | | | | | | |
|---|---|---|---|---|---|---|---|---|
| Component | I | II | III | IV | V | VI | VII | VIII |
| Gum Blend++ (GFS, Kelko, Div. Merck & Co.) | | | 70 | | | | | |
| Cross-linked Poly(Sodium, acrylate), (Favorsab ®, Stockhausen) | | | | 70 | | | | |
| Cross-linked Ionic Polyacrylate (Permasorb ® AG, National Starch) | | | | | 70 | | | |
| Cross-linked Ionic Polyacrylate (Permasorb ® ZO, National Starch) | | | | | | 30 | | |
| Starch Polyacrylate (35A 100, Grain Products) | | | | | | | 70 | |
| Cross-linked Carboxymethylcellulose, (Akucell ® SW, Enka Industries) | | | | | | | | 80 |
| Liquid Polyhydroxy Compound | | | | | | | | |
| Glycerol | | 100 | | | | 100 | | |
| Ethylene Glycol | 100 | | 100 | 100 | 100 | | 100 | 100 |

+Hydrolyzed polyacrylonitrile grafted to starch
++Blend of xanthan gum, locust bean gum and guar gum The products having the compositions identified in Table A are employed to coat substrates to product absorbent articles as follows:

The products having the compositions of Examples I, IV, and VI are employed to coat diaper topsheet materials (a) a nonwoven fabric sheet comprising 1.5 to 3.0 denier rayon and containing 20 to 35 percent acrylate ester copolymer binder, and having a weight of about 15 to 19 grams per square yard, and (b) a nonwoven fabric sheet comprising 35 to 64 percent 1.5 to 3.0 denier polyester fiber, 14 to 40 percent 1.5 to 3.0 denier rayon fibers and 20 to 30 percent of the same acrylate ester copolymer binder, and having a weight of about 25 to 35 grams per square yard. The modified topsheet materials when employed to produce diapers or when employed as an insert in disposable diapers produce diapers having superior absorption properties and in which the particulate absorbents are found to be substantially completely immobile.

The products having the compositions of Examples III and VII are employed to saturate creped paper. The modified papers are employed to produce inserts for absorbent bed paddings.

The products having the compositions of Examples V and VIII are employed to coat polyethylene film to be employed as backing for disposable diapers. The modified backing is then overlaid with fluffed cellulose fibers forming a laminate then with overlaid with nonwoven fabric web to produce a superior absorbent diaper.

The product having the composition of Examples II is employed to coat nonwoven fabric of rayon, above described, and thereafter laminated with the same material to use as inserts for napkins and bandages.

In use, each of the products exhibits superior absorption properties attributable to the particulate absorbent borne thereon. Further it is found that the particulate absorbent materials are not dislodged on storage, shipping or use.

EXAMPLES X-XVII

Foamable compositions as set forth in Table B are first prepared by first mixing together at ambient temperature the appropriate absorbent and blowing agent, thereafter adding the appropriate liquid polyhydroxy organic compound, and mixing to a smooth dispersion.

TABLE B

|  | Amount of Components (parts by weight) Examples | | | | | | | |
|---|---|---|---|---|---|---|---|---|
| Component | X | XI | XII | XIII | XIV | XV | XVI | XVII |
| Absorbent | | | | | | | | |
| Starch Polyacrylate (SPC 502S, Henkel) | | | | | | | 50 | |
| Starch Polyacrylate (Stasorb ®, A. E. Staley) | | | | | | 50 | | |
| Cross-linked Ionic Polyacrylate (Permasorb ® AG, National Starch) | 50 | 75 | 50 | | | | | |
| Polyacrylate (Sanwet ®, Sanyo) | | | | | 50 | | | |
| Polyacrylate (Aqua-Keep, Mitsubishi) | | | | 50 | | | | |
| Cellulose Polyacrylate* | | | | | | | | 50 |
| Polyhydroxy Compound | | | | | | | | |
| Glycerol | 100 | | 100 | 100 | 100 | | | |
| Ethylene Glycol | | 100 | | | | 100 | 100 | 100 |
| Blowing Agent | | | | | | | | |
| Celogen ® OT[1] | | | 5 | | | | | |
| Celogen ® TSH[2] | | 5 | | | | | | 5 |
| Celogen ® AZ[3] | | | | | 5 | 5 | | |

TABLE B-continued

| Component | Amount of Components (parts by weight) Examples | | | | | | | |
|---|---|---|---|---|---|---|---|---|
| | X | XI | XII | XIII | XIV | XV | XVI | XVII |
| Sodium Bicarbonate | 5 | 10 | | | | 5 | | |

*Prepared according to U.S. Pat. No. 3,889,678
[1] p,p-Oxybisbenzene sulfonyl hydrazide;
[2] p-Tolene sulfonyl hydrazide;
[3] Azodicarbonamide; all products of Uniroyal Chemical In separate operations, portions of each composition are treated in the following manner: (a) knife-coated onto a release-coated paper, (b) knife-coated onto a polyethylene film, and (c) poured into the space between the inner glass and outer metal walls of a dual-wall container until about one-tenth of the space is filled. The treated compositions are allowed to stand at ambient temperature whereupon foaming occurs in a few hours and there are obtained (a) foam sheets from the compositions which have been knife-coated onto release coated paper; (b) foam-coated film from compositions which have been knife-coated onto polyethylene film; and (c) foam in the space near the bottom portion of the double wall container.

The operation is repeated except that the treated samples are exposed to a temperature of about 275° F. for ten seconds to obtain the corresponding foam products.

When about 100 grams of water is applied to foam (about 10 gram size) in each of the foregoing examples, the foam swells instantaneously taking up the water substantially completely.

EXAMPLE XVIII

A foamable composition is prepared by mixing together at ambient temperature 80 parts of starch polyacrylate (Stasorb ®) and 5 parts of sodium bicarbonate, and then adding and mixing 100 parts of glycerol. In separate operations, the composition is knife-coated onto (a) nonwoven cellulosic fabric, (b) polyethylene film, and (c) thin layer of wood pulp material as substrates. The coated substrates are exposed to a temperature of 300° F. for a few seconds to obtain foam coated substrates. The foam coated substrates are then slit into sizes suitable for absorbent articles.

When water is applied to the articles comprising foam coated substrates, there is instantaneous removal of free-standing water and swelling of the foam.

I claim:

1. An absorbent-immobilizing composition in liquid form comprising:
   (a) at least about 25 to no greater than about 125 parts of a particulate water-insoluble, water-swellable absorbent polymer having a gel capacity of at least 10, said absorbent polymer being other than a hydrolyzed starch/polyacrylonitrile graft copolymer, and
   (b) 100 parts by weight of a liquid polyhydroxy organic compound having vicinal hydroxy groups.

2. A composition according to claim 1 in which the particulate absorbent polymer is employed in an amount of from about 40 to about 80 parts.

3. An absorbent immobilizing foam forming composition comprising:
   (a) at least about 25 to no greater than about 125 parts of a particulate water-insoluble, water-swellable absorbent polymer having a gel capacity of at least ten,
   (b) 100 parts by weight of the liquid polyhydroxy organic compound having vicinal hydroxy groups, and
   (c) 2 to 30 parts by weight of a non-solid blowing agent.

4. An absorbent film or sheet product prepared by coating or casting an absorbent-immobilizing composition comprising from about 25 to 125 parts of particulate water-insoluble, water-swellable absorbent polymer having a gel capacity of at least 10, said absorbent polymer being other than a hydrolyzed starch/polyacrylonitrile graft copolymer, in 100 parts of liquid polyhydroxy organic compound having vicinal hydroxy groups, and thereafter subjecting the coated or cast liquid to conditions for solidification by allowing to stand at a temperature up to about 175° F. from about 30 minutes to 24 hours or heating at temperatures of 175° F. to 450° F. for from a few seconds up to about 15 minutes.

5. An absorbent product according to claim 4 which is a foam sheet and which has been prepared by including 2 to 30 parts of blowing agent to the composition of claim 4.

6. An absorbent foam product prepared by mixing together a solid, particulate, water-insoluble, water-swellable polymer having a gel capacity of at least 10, a non-solid blowing agent, and a liquid polyhydroxy organic compound having vicinal hydroxy groups and allowing the mixture to foam.

7. A product according to claim 6 wherein the particulate water-insoluble, water-swellable absorbent polymer is starch polyacrylate.

8. A product according to claim 6 wherein the solid particulate water-insoluble, water-swellable absorbent polymer is cellulose polyacrylate.

9. A product according to claim 6 wherein the solid, particulate water-insoluble, water-swellable absorbent polymer is polyacrylate.

10. A product according to claim 6 wherein the liquid polyhydroxy compound is glycerol.

11. A product according to claim 6 wherein the liquid polyhydroxy compound is ethylene glycol.

12. A product according to claim 6 wherein from about 40 to 80 parts by weight the particulate, water-insoluble, water-swellable polymer and from about 2 to 30 parts by weight of the blowing agent are employed for every 100 parts by weight of liquid polyhydroxy organic compound.

13. A product according to claim 6 wherein the water-insoluble water-swellable polymer is polyacrylate and the liquid polyhydroxy organic compound is ethylene glycol.

14. A product according to claim 6 wherein the water-insoluble water-swellable polymer is polyacrylate and the liquid polyhydroxy organic compound is glycerol.

15. A product according to claim 6 wherein the mixture is allowed to foam by standing at ambient temperature for from about 1 to about 24 hours.

16. A product according to claim 6 wherein the mixture is allowed to foam by subjecting the mixture to a temperature in the range of about 175° F. to 450° F. for from a few seconds to a few minutes.

17. A process for decreasing the mobility of particulate absorbent in absorbent articles and improving moisture transport therein which comprises applying an absorbent-immobilizing composition comprising
   (a) at least about 25 to no greater than about 125 parts of a particulate water-insoluble water-swellable absorbent polymer having a gel capacity of at least 10, said absorbent polymer being other than a hydrolyzed starch/polyacrylonitrile graft copolymer, and
   (b) 100 parts by weight of a liquid polyhydroxy organic compound having vicinal hydroxy groups, onto a substrate or casting surface as a liquid layer to form a liquid film and thereafter subjecting the liquid film to solidifying conditions for time sufficient to transform the liquid film to an absorbent-bearing solidified structure.

18. A process according to claim 17 in which the liquid film is heated at temperatures in the range of from 175° to 450° F. for from about 1 to 60 seconds.

19. A process according to claim 17 in which the liquid film is allowed to stand at ambient temperature for from about 60 minutes to about 24 hours.

20. A process according to claim 17 in which the liquid polyhydroxy organic compound is glycerol.

21. A process according to claim 17 in which the liquid polyhydroxy organic compound is ethylene glycol.

22. An absorbent film formed by coating or casting a liquid absorbent-immobilizing composition comprising from about 25 to 125 parts of a solid particulate water-insoluble, water-swellable absorbent polymer having a gel capacity of at least 10, said absorbent polymer being other than a hydrolyzed starch/polyacrylonitrile graft copolymer in 100 parts of liquid polyhydroxy organic compound having vicinal hydroxy groups and thereafter heating the resulting liquid film at temperatures of from about 175° to 450° F. for from seconds few seconds to about 15 minutes.

23. An immobilized absorbent-bearing product of particulate water-insoluble, water-swellable absorbent polymer having a gel capacity of at least 10, said absorbent polymer being other than a hydrolyzed starch/polyacrylonitrile graft copolymer, and a liquid polyhydroxy organic compound having vicinal hydroxy groups.

24. An absorbent-immobilizing composition in liquid form comprising:
   (a) at least about 25 to no greater than about 125 parts of a particulate water-insoluble, water-swellable absorbent polymer having a gel capacity of at least 10, said absorbent polymer being other than a hydrolyzed starch/polyacrylonitrile graft copolymer said absorbent polymer being selected from polyacrylate modified cellulose, synthetic cross-linked polyacrylate cross-linked carboxymethylcellulose, cross-linked poly(alkylene oxide), a blend of gums selected from guar, xanthan and locust bean gums, and
   (b) 100 parts by weight of a liquid polyhydroxy organic compound having vicinal hydroxy groups.

25. An absorbent-immobilizing composition in liquid form comprising:
   (a) at least about 25 to no greater than about 125 parts of a particulate water-insoluble, water-swellable absorbent polymer having a gel capacity of at least 10 said absorbent polymer being other than a hydrolyzed starch/polyacrylonitrile graft copolymer, and
   (b) 100 parts by weight of a liquid polyhydroxy organic compound, said liquid polyhydroxy organic compound being ethylene glycol.

26. An absorbent-immobilizing composition in liquid form comprising:
   (a) at least about 25 to no greater than about 125 parts of a particulate water-insoluble, water-swellable absorbent polymer having a gel capacity of at least 10 said absorbent polymer being other than a hydrolyzed starch/polyacrylonitrile graft copolymer, said absorbent polymer being synthetic cross-linked polyacrylate, and
   (b) 100 parts by weight of a liquid polyhydroxy organic compound having vicinal hydroxy groups.

27. A composition according to claim 26 in which the liquid polyhydroxy organic compound is ethylene glycol.

28. A composition according to claim 26 in which the liquid polyhydroxy organic compound is glycerol.

* * * * *